(12) United States Patent
Hawkins et al.

(10) Patent No.: US 8,206,143 B2
(45) Date of Patent: Jun. 26, 2012

(54) MODULAR ARTICULATING CEMENT SPACER

(75) Inventors: H. Gene Hawkins, Warsaw, IN (US); William Hartman, Warsaw, IN (US); Kristen Martin, Wakarusa, IN (US); Nathan A. Winslow, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 583 days.

(21) Appl. No.: 12/390,084

(22) Filed: Feb. 20, 2009

(65) Prior Publication Data
US 2009/0175978 A1 Jul. 9, 2009

Related U.S. Application Data

(63) Continuation-in-part of application No. 11/955,601, filed on Dec. 13, 2007, now Pat. No. 7,637,729.

(51) Int. Cl.
*B28B 7/00* (2006.01)
(52) U.S. Cl. ........ 425/214; 425/226; 425/442; 425/460; 425/470
(58) Field of Classification Search .......... 425/214, 425/218, 226, 460, 470, 442
See application file for complete search history.

(56) References Cited

U.S. PATENT DOCUMENTS

| | | |
|---|---|---|
| 1,525,126 A | 2/1925 | Goldstein |
| 2,347,567 A | 4/1944 | Kresse |
| 2,527,992 A | 10/1950 | Greenberg |
| 2,954,144 A | 9/1960 | Elam et al. |
| 3,014,614 A | 12/1961 | Carroll et al. |
| 3,102,536 A | 9/1963 | Rose et al. |
| 3,144,966 A | 8/1964 | Cook |
| 3,580,484 A | 5/1971 | Schneider |
| 3,774,244 A | 11/1973 | Walker |
| 3,857,932 A | 12/1974 | Shepherd et al. |
| 3,882,858 A | 5/1975 | Klemm |
| 3,907,245 A | 9/1975 | Linder |
| 3,964,106 A | 6/1976 | Hutter, Jr. et al. |
| 3,966,166 A | 6/1976 | Elliott |
| 4,059,684 A | 11/1977 | Gross et al. |
| 4,191,740 A | 3/1980 | Heusser et al. |
| 4,235,578 A | 11/1980 | Cosmi |
| 4,322,398 A | 3/1982 | Reiner et al. |
| 4,375,810 A | 3/1983 | Belykh et al. |
| 4,456,573 A * | 6/1984 | Ragazzini et al. .............. 264/53 |

(Continued)

FOREIGN PATENT DOCUMENTS
DE 297039717 9/1998
(Continued)

OTHER PUBLICATIONS

International Search Report and Written Opinion mailed Sep. 20, 2010 for PCT/US2010/024586 which claims benefit of U.S. Appl. No. 12/390,084, filed Feb. 20, 2009, which claims benefit of U.S. Appl. No. 11/955,601, filed Dec. 13, 2007.

(Continued)

*Primary Examiner* — Yogendra Gupta
*Assistant Examiner* — Emmanuel S Luk
(74) *Attorney, Agent, or Firm* — Harness, Dickey (57) ABSTRACT

The present teachings provide a modular articulating cement spacer mold for forming a temporary implant comprising a mold first portion; a mold second portion; a hinge region connecting the mold first portion and mold second portion; and a self-securing device to removably secure and separate the mold first portion and the mold second portion. Other modular articulating cement spacer molds are also provided.

14 Claims, 10 Drawing Sheets

U.S. PATENT DOCUMENTS

| | | | |
|---|---|---|---|
| 4,550,723 A | | 11/1985 | Belykh et al. |
| 4,579,700 A | * | 4/1986 | Cavender ............... 264/46.4 |
| 4,581,028 A | | 4/1986 | Fox, Jr. et al. |
| 4,610,692 A | | 9/1986 | Eitenmuller et al. |
| 4,615,705 A | | 10/1986 | Scales et al. |
| 4,624,673 A | | 11/1986 | Meyer |
| 4,721,390 A | | 1/1988 | Lidgren et al. |
| 4,739,963 A | | 4/1988 | Parmacek et al. |
| 4,749,585 A | | 6/1988 | Greco et al. |
| 4,750,905 A | | 6/1988 | Koeneman et al. |
| 4,797,282 A | | 1/1989 | Wahlig et al. |
| 4,803,028 A | | 2/1989 | Torossian et al. |
| 4,853,225 A | | 8/1989 | Wahlig et al. |
| 4,869,906 A | | 9/1989 | Dingeldein et al. |
| 4,882,149 A | | 11/1989 | Spector |
| 4,888,024 A | | 12/1989 | Powlan |
| 4,900,546 A | | 2/1990 | Posey-Dowty et al. |
| 4,917,589 A | | 4/1990 | Manderson |
| 4,919,666 A | | 4/1990 | Buchhorn et al. |
| 4,950,300 A | | 8/1990 | Langlais |
| 5,015,257 A | | 5/1991 | Crowninshield et al. |
| 5,033,712 A | | 7/1991 | Ravet |
| 5,061,286 A | | 10/1991 | Lyle |
| 5,098,620 A | | 3/1992 | Bradley et al. |
| 5,108,452 A | | 4/1992 | DeMane et al. |
| 5,123,927 A | | 6/1992 | Duncan et al. |
| 5,133,771 A | | 7/1992 | Duncan et al. |
| 5,141,521 A | | 8/1992 | Wenner |
| 5,236,457 A | | 8/1993 | Devanathan |
| 5,328,262 A | | 7/1994 | Lidgren et al. |
| 5,370,221 A | | 12/1994 | Magnusson et al. |
| 5,501,520 A | | 3/1996 | Lidgren et al. |
| 5,501,687 A | | 3/1996 | Willert et al. |
| 5,538,514 A | | 7/1996 | Hawkins |
| 5,858,020 A | | 1/1999 | Johnson et al. |
| 5,951,160 A | | 9/1999 | Ronk |
| 6,146,419 A | | 11/2000 | Eaton |
| 6,155,812 A | | 12/2000 | Smith et al. |
| 6,258,089 B1 | | 7/2001 | Campbell et al. |
| 6,286,670 B1 | | 9/2001 | Smith |
| 6,352,659 B1 | * | 3/2002 | Clark et al. ............... 264/51 |
| 6,361,731 B1 | | 3/2002 | Smith et al. |
| 7,018,089 B2 | | 3/2006 | Wenz et al. |
| 7,396,495 B2 | * | 7/2008 | Friesner ............... 264/46.4 |
| 7,878,785 B2 | * | 2/2011 | Cathcart et al. ............... 425/4 R |
| 2002/0001694 A1 | * | 1/2002 | Wetzel ............... 428/131 |
| 2003/0065398 A1 | | 4/2003 | Cueille et al. |
| 2003/0122285 A1 | * | 7/2003 | Crane et al. ............... 264/511 |
| 2003/0155381 A1 | | 8/2003 | Chan |
| 2005/0004680 A1 | | 1/2005 | Saladino et al. |
| 2005/0027302 A1 | | 2/2005 | Cueille et al. |
| 2005/0143828 A1 | | 6/2005 | Collins et al. |
| 2006/0109737 A1 | | 5/2006 | Wilander |
| 2007/0016215 A1 | | 1/2007 | Wilander et al. |
| 2007/0026098 A1 | * | 2/2007 | Lemaistre et al. ............ 425/170 |
| 2007/0211563 A1 | | 9/2007 | De Vries |
| 2007/0222114 A1 | | 9/2007 | Ziran et al. |
| 2009/0234034 A1 | * | 9/2009 | Blanco ............... 521/48 |
| 2010/0046315 A1 | | 2/2010 | Merkhan et al. |
| 2011/0064840 A1 | * | 3/2011 | Borgatti et al. ............... 425/541 |

FOREIGN PATENT DOCUMENTS

| | | |
|---|---|---|
| EP | 0016480 A1 | 10/1980 |
| EP | 0129531 A2 | 12/1984 |
| EP | 166724 | 1/1986 |
| EP | 1005900 A2 | 6/2000 |
| EP | 2014429 A2 | 1/2009 |
| FR | 2639820 A1 | 6/1990 |
| FR | 2898039 | 9/2007 |
| WO | WO-8705492 A1 | 9/1987 |
| WO | WO-9851240 | 12/1998 |

OTHER PUBLICATIONS

Booth Jr & Lotke, "The Results of Spacer Block Technique in Revision of Infected Total Knee Arthroplasty," Clinical Orthopaedics and Related Research, No. 248, Nov. 1989; pp. 57-60.

Cohen, Hozack, Cuckler, Booth "Two-Stage Reimplantation of Septic Total Knee Arthroplasty;" The Journal of Arthroplasty, vol. 3, No. 4, Dec. 1988; pp. 369-377.

Flick, Herbert, Goodell & Kristiansen; Clinical Orthopaedics & Related Research, "Noncommercial Fabrication of Antibiotic-impregnated Polymethylmethacrylate Beads;" No. 223, Oct. 1987; pp. 282-286.

Goodell, Flick, Hebert & Howe, "Preparation and Release Characteristics of Tobramycin-impregnated Polymethylmethacrylate Beads;" Americal Journal of Hospital Pharmacy, vol. 43, Jun. 1986; pp. 1454-1461.

Hofmann, Kane, Tkach, Plaster & Camargo; Clinical Orthopedics & Related Research, "Treatment of Infected Total Knee Arthroplasty Using an Articulating Spacer;" Clinical Orthopaedics and Related Research; copyright 1995 Lippincott-Raven Publishers,No. 321, pp. 45-54.

Wilde & Ruth, "Two Stage Reimplantation in Infected Total Knee Arthroplasty;" Clinical Orthopaedics & Related Research, No. 236, Nov. 1998;pp. 23-35.

Invitation to Pay Additional Fees including Results of the Partial International Search mailed Jul. 1, 2010 for PCT/US2010/024586 filed Feb. 18, 2010 claiming benefit of U.S. Appl. No. 12/390,084, filed Feb. 20, 2009, which claims benefit of U.S. Appl. No. 11/955,601, filed Dec. 13, 2007.

Biomet Orthopedics, Inc., "The Optivac® Vacuum Mixing System, Intelligent Simplicity," brochure, 2000 (12 pages).

Biomet, "Mixing and Delivery: Optivac®", pp. 1-2, available at http://www.bonecement.com/index.php?id=16933, printed Jul. 15, 2008.

Biomet, "Optivac® Procedure Set," pp. 1-2, available at http://www.bonecement.com/index.php?id=17149, last visited Jul. 15, 2008.

Biomet, Inc., "Optivac® Fusion™ Vacuum Mixing Bowl," pp. 1-2, 2001-2008, available at http://www.biomet.com/hcp/prodpage.cfm?c=0F&p=090505 (printed Feb. 4, 2008).

Biomet, Inc., "Optivac® Vacuum Mixing System," 2001-2008, pp. 1-2, available at http://www.biomet.com/hcp/prodpage.cfm?c=0F&p=0A0403 (printed Feb. 4, 2008).

DePuy Orthopaedics, Inc., "Prostalac Hip Temporary Prosthesis", pp. 1-2, 2001, available at http:/www.fda.gov/cdrh/mda/docs/h000004.html, printed Feb. 8, 2007 (2 pages).

DePuy, "Prostalac® Hip", pp. 1-2, 2005-2006, available at http://www.jnjgateway.com/home.jhtml?page=viewContent&contentId=09008b98800540d1&loc=USENG, printed Feb. 8, 2007 (2 pages).

Exactech, Inc., "InterSpace® Hip," p. 1, available at http://www.exac.com/products/cement-spacers/interspace-hip, last visited Jul. 15, 2008.

International Search Report and Written Opinion for PCT/US2008/085529 mailed Mar. 17, 2009 claiming priority to U.S. Appl. No. 11/955,601, filed Dec. 13, 2007.

Johnson & Johnson, "Prostalac® Hip Essential Product Information," p. 1-3, available at http://www.jnjgateway.com/home.jhtml?contentID=09008b9880054123&loc=USENG&page=viewContent, last visited Jul. 15, 2008.

International Search Report and Written Opinion mailed Dec. 21, 2009 for PCT/US2009/054613 claiming benefit of U.S. Appl. No. 12/196,394, filed Aug. 22, 2008.

International Preliminary Report on Patentability and Written Opinion mailed Sep. 1, 2011 for PCT/US2010/024586 which claims benefit of U.S. Appl. No. 12/390,084, filed Feb. 20, 2009, which claims benefit of U.S. Appl. No. 11/955,601, filed Dec. 13, 2007.

* cited by examiner

MODULAR ARTICULATING CEMENT SPACER

CROSS-REFERENCE TO RELATED APPLICATIONS

This application is a continuation-in-part of U.S. patent application Ser. No. 11/955,601 filed on Dec. 13, 2007. The entire disclosure of the above application is incorporated herein by reference.

FIELD

The present disclosure relates to a spacer mold, and more particularly, to a modular articulating two-stage cement hip spacer mold.

BACKGROUND

A natural joint may undergo degenerative changes due to a variety of etiologies. When these degenerative changes become so far advanced and irreversible, it may ultimately become necessary to replace the natural joint with a joint prosthesis. However, due to any number of reasons, a small portion of patients that undergo such orthopedic surgical procedures may suffer from infections at the surgical site and generally around the implanted joint prosthesis. In order to cure such an infection in a two-stage re-implantation, the implanted joint prosthesis may be removed, the site is thoroughly debrided and washed, antibiotics are applied to the infected site via a temporary implant until the infection is eliminated, and a new revision type joint prosthesis is then implanted during a subsequent orthopedic surgical procedure.

Accordingly, there is a need for apparatus and methods to facilitate two-stage re-implantation which expedite healing at the site, provide a better fitting implant, reduce the amount of time a patient is bedridden, increase the efficiency of the surgical procedure while reducing the surgical time and cost, eliminate any re-cleaning or re-sterilizing steps, and create a customizable procedure.

SUMMARY

This section provides a general summary of the disclosure, and is not a comprehensive disclosure of its full scope or all of its features.

In various embodiments a modular articulating cement spacer mold for forming a temporary implant is provided. The modular articulating cement spacer mold comprises a first mold, a second mold, and a connecting hinge. In various embodiments, the modular articulating cement spacer mold can include a self-cleaning mechanism, a self-securing device, or a ventilation forming feature.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The following description is merely exemplary in nature and is not intended to limit the present disclosure, application, or uses. Although certain examples and surgical methods disclosed herein are in conjunction with a temporary hip implant, it is understood that the molds and surgical methods disclosed herein can be used in any orthopedic revision surgery for any area in the patient.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
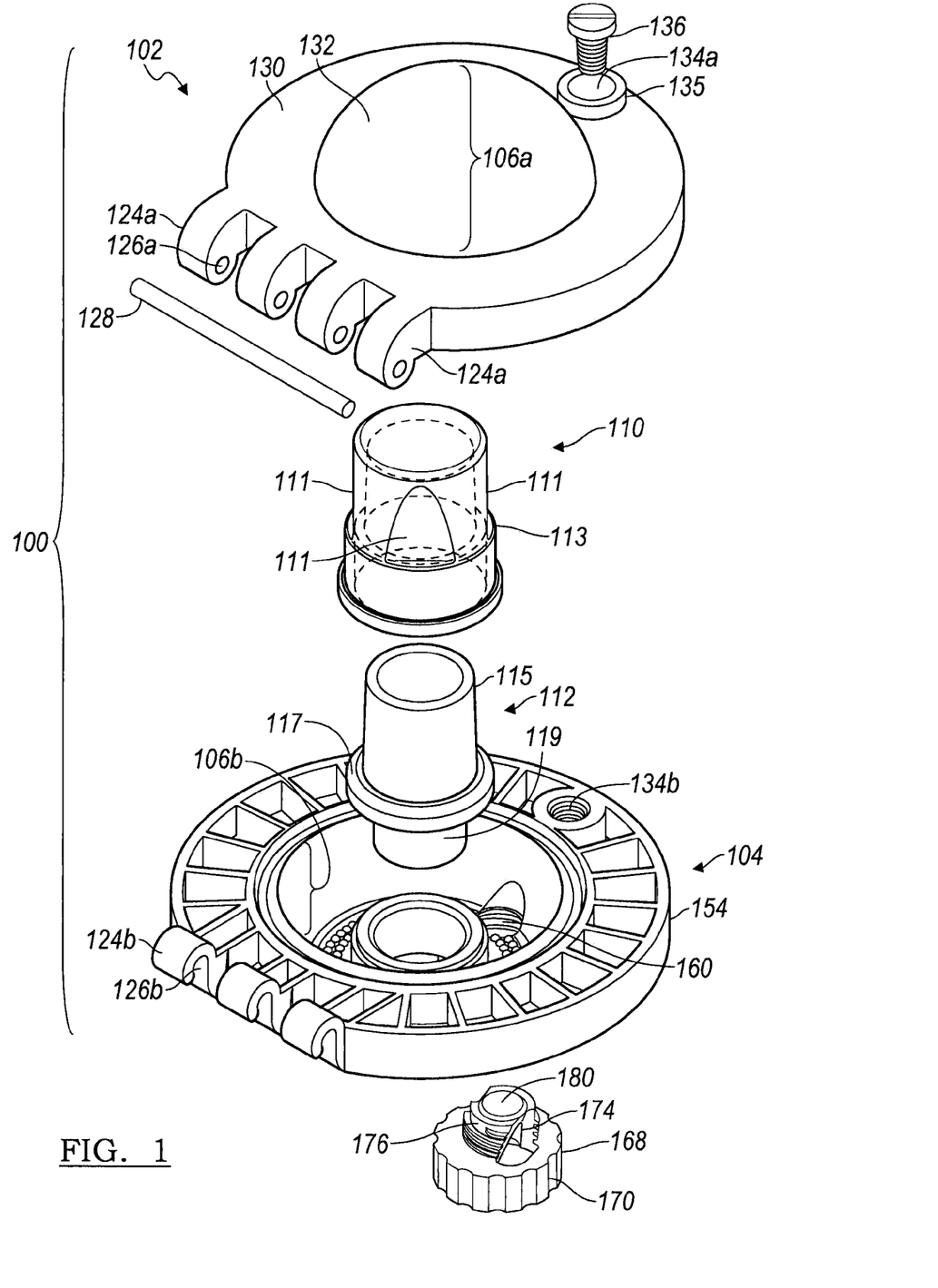
FIG. 1 depicts an exploded view of a head mold component and various connection features according to various embodiments.
Figure 6:
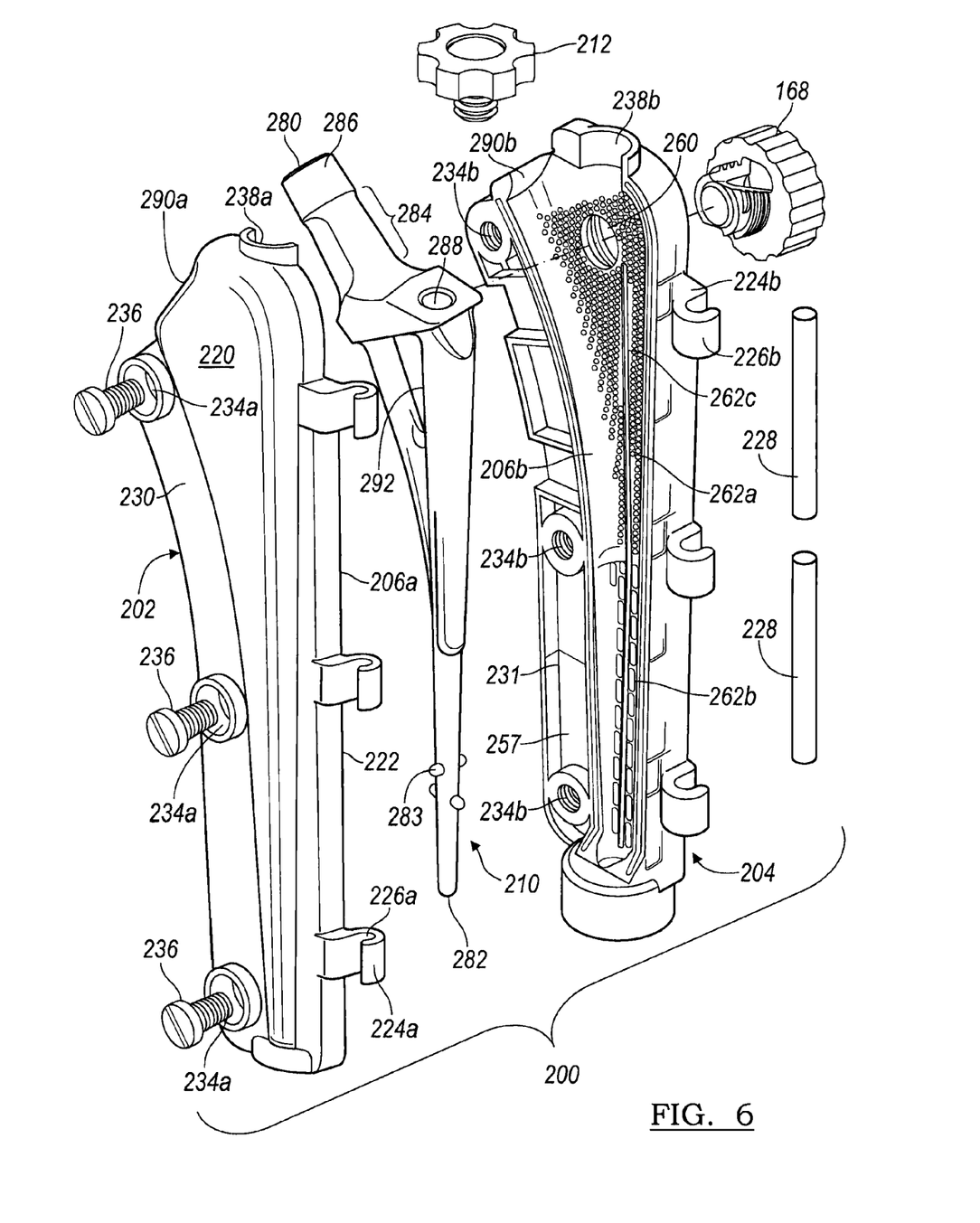
FIG. 6 depicts an exploded view of a stem mold component and various connection features according to various embodiments.

Referring to FIGS. 1 and 6, the present teachings provide a modular articulating cement spacer mold for forming a temporary implant. The system includes a head component mold 100, as shown in FIG. 1, and a stem component mold 200, as shown in FIG. 6. It is understood that various features from the head component mold 100 and the stem component mold 200 can be interchanged within the scope of the present teachings. The modularity of the present teachings allows the surgeon to create a highly customized implant based on both the head and the stem size needs of the patient. This is beneficial in revision surgery where the condition of either the acetabulum or the femur may differ to the extent that a monolithic temporary implant may not best meet the needs of the patient. The present temporary implants are optimized for strength and reinforce the high stress areas along the neck of the implant. It is understood that the present teachings, while illustrative of a hip implant, can also be used for other orthopedic uses, including, for example, a shoulder or a knee.

Figure 9A:
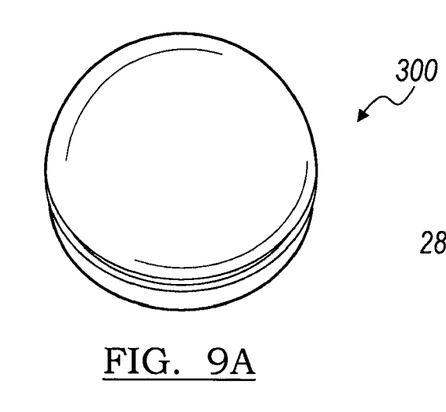
FIGS. 9A-9B depict a temporary femoral head implant according to various embodiments.
Figure 9B:
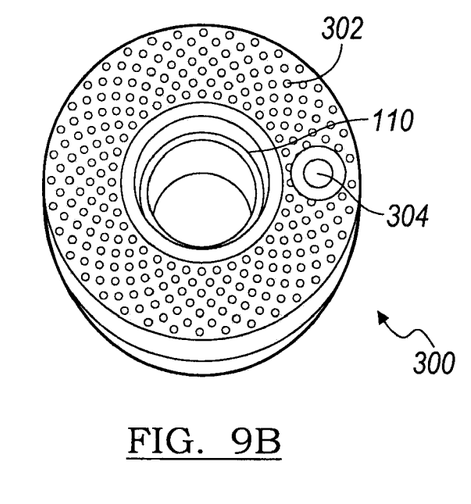
Figure 10:
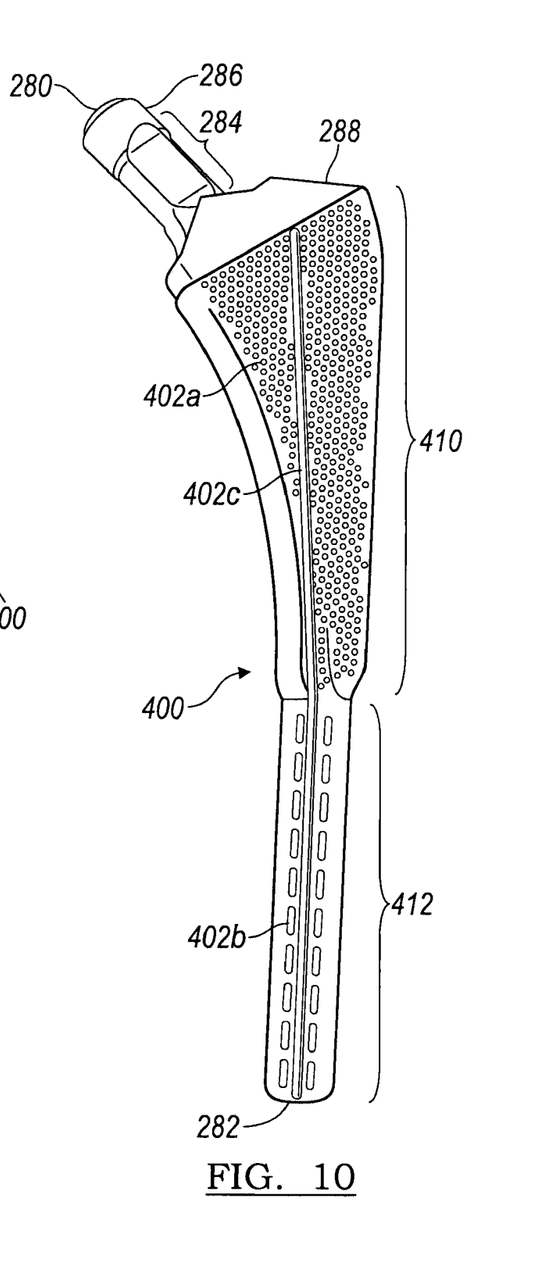
FIG. 10 depicts a temporary femoral stem implant according to various embodiments.

The molds 100 and 200 can be formed from any biocompatible material including various polymers. In various embodiments, the polymeric material can be sufficiently rigid to provide structure to the resultant implant components 300 and 400 as shown in FIGS. 9A-10. In various embodiments, the molds 100 and 200 are formed from a plastic, such as polyethylene, polypropylene, or polyetheretherketone (PEEK) including carbon reinforced PEEK. Such materials have a sufficiently high stiffness such that the molds 100 and 200 will not sag or be unintentionally deformed upon handling. It is understood that other materials can also be used to form the molds 100 and 200, including silicone, for example, Dow Q7-4780 or any other 80 durometer silicone or including rubber. It should be noted that the material selected should generally not adversely react with the bone cement and antibiotic selected. In various embodiments, the materials used may be transparent or partially transparent to allow an operator to observe the formation of the temporary implant. The head component mold portions 102 and 104 or the stem component mold portions 202 and 204 can be formed by various conventional molding techniques such as injection molding, compression molding, blow molding, spin casting, etc.

Turning to FIG. 1, the head component mold 100 can be used to form the temporary implant head component 300 as shown in FIGS. 9A and 9B. Returning to FIG. 1, the head component mold 100 includes a first head component mold portion 102 and a second component mold portion 104. The first head component mold portion 102 and the second component mold portion 104 each generally forms a portion of a "clamshell" and define cavity portions 106a and 106b, respectively, such that upon connecting and closing the portions 102 and 104. The area between the cavity portions 106a and 106b accommodates the cement, a head connector 110, and a head connector alignment member 112. It is understood that while the head component mold 100 is depicted as connecting along a sagittal plane and the stem component mold 200 is depicted as connecting along the coronal plane, as shown in FIG. 6, the placements are not limiting and are merely exemplary. Modifications to the planar alignment (i.e.: either sagittal alignment or both coronal alignment, for example) are within the scope of the present teachings. Further, the present disclosure is not limited to embodiments where there are only a first mold portion and a second mold portion. It is understood that any plurality of components can be used to form the mold portion.

Figure 2A:
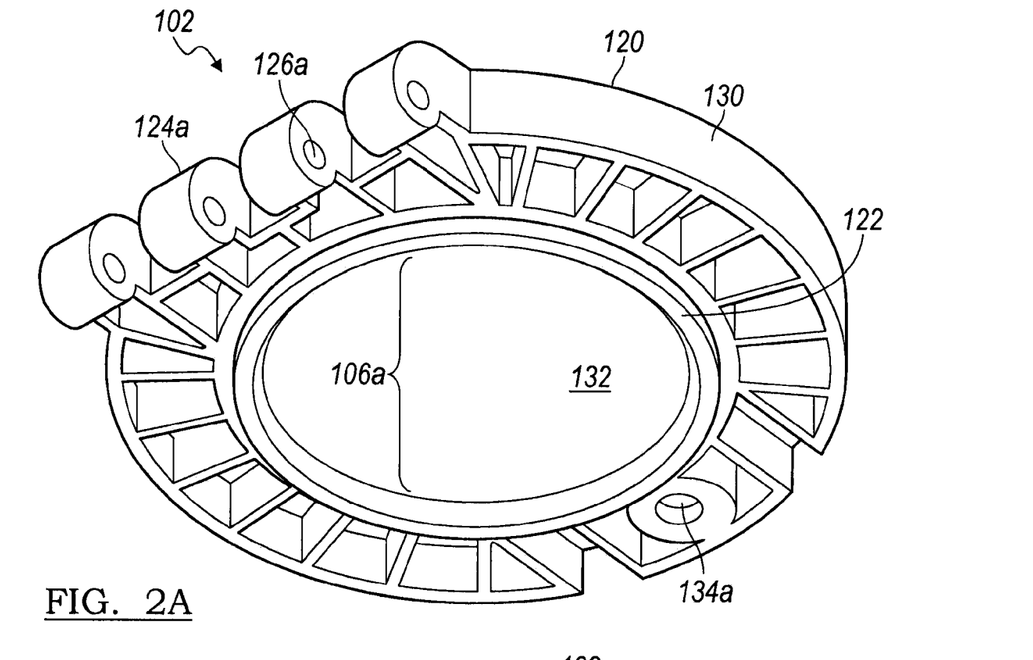
FIG. 2A depicts a interior view of a first portion of the head mold component according to various embodiments.
Figure 2B:
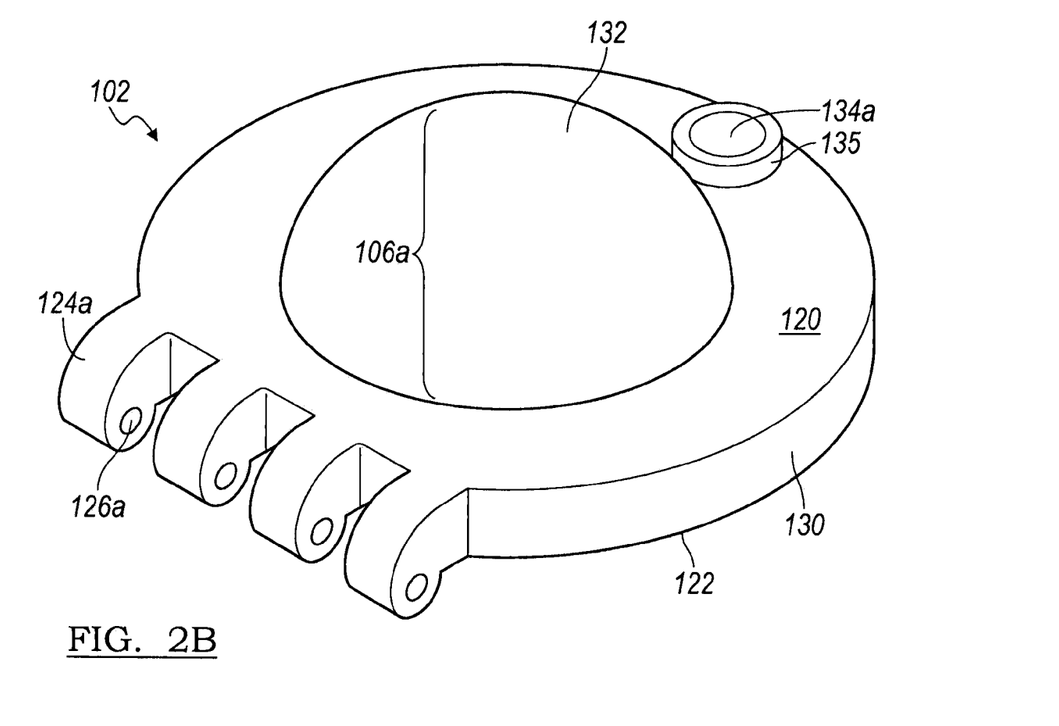
FIG. 2B depicts an exterior view of a first portion of the head mold component according to various embodiments.

Referring to FIGS. 1 and 2A-2B, the head component first mold portion 102 includes an outer surface 120, an inner surface 122, and connection components 124a which further defines a series of openings 126a therein to accommodate a connection component pin 128 (only shown in FIG. 1). It should be noted that the hinge pin 128 can be molded into the openings 126a. Also, as will be illustrated below, it is understood that the hinge pin 128 can also be formed into separate pieces. Minor modifications of the hinge are within the scope of the present teachings. The perimeter or edge 130 of the head component first mold portion 102 surrounds a raised dome region 132 which extends upwardly from the outer surface 120. The raised region 132 provides the semi-hemispherical shape to the resultant implant as shown in FIG. 9A.

Figure 11A:
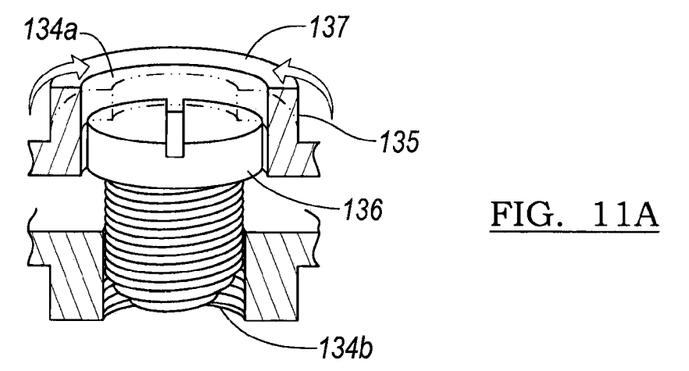
FIGS. 11A-11B depict a self-separating mechanism according to various embodiments.
Figure 11B:
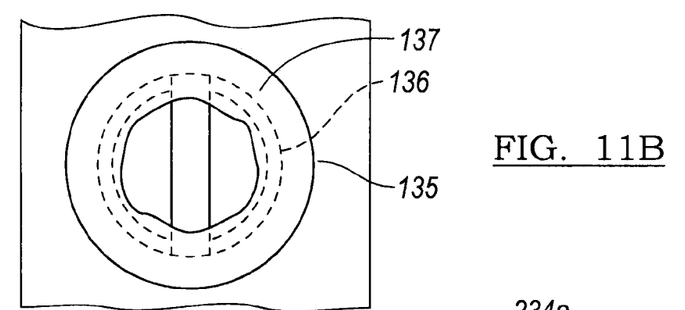

Returning to FIGS. 1 and 2A-2B, on the end of the edge 130 which is opposite to the end having the connection component 124b, the head component first mold portion 102 defines an opening 134a to accommodate a screw 136 to secure the head component first mold portion 102 with the head component second mold portion 104. As best shown in FIGS. 11A and 11B, the opening 134a includes a ledge 135 which is deformable and can be bent over a region of the screw 136 to form a fold-over region 137 (FIGS. 11A and 11B) to rotatably capture the screw 136 and provide a self-securing device or a dual securing and separating mechanism to combine the first mold portion 102 and second mold portion 104 or to separate them. In various embodiments, the fold over region 137 may be a separately molded piece that is secured to the opening 134a. For example, the fold over region 137 may be sonically welded to the opening 134a.

In an exemplary use, advancing the screw 136 into the opening 134a and securing with the threads 134b secures the first mold portion 102 and second mold portion 104 together. This securement can be further supported by forming a fold-over region 137 over a portion of the screw 136. By fixing the ledge 135 over the screw 136 to form a fold-over region 137, the operator is provided a bearing surface against which the screw 136 cannot advance. When the operator rotates the screw 136 as to back it out from the threaded opening 134b, the ledge 135 and fold-over region 137 trap the screw 136, prevent the backward rotation of the screw 136 from removing the screw 136, and instead help pry apart the first mold portion 102 and second mold portion 104.

Figure 3A:
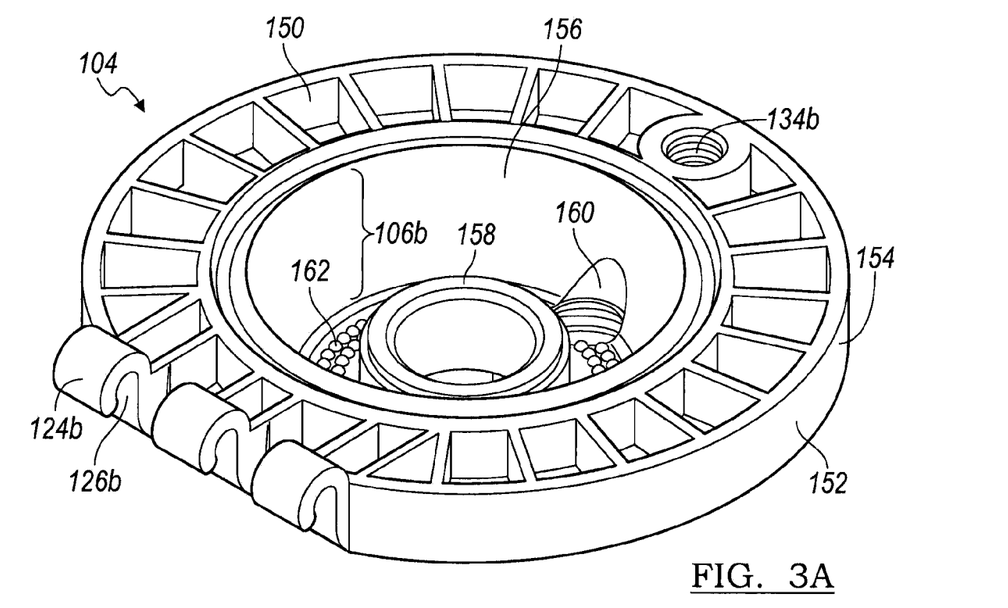
FIG. 3A depicts an interior view of a second portion of the head mold component according to various embodiments.
Figure 3B:
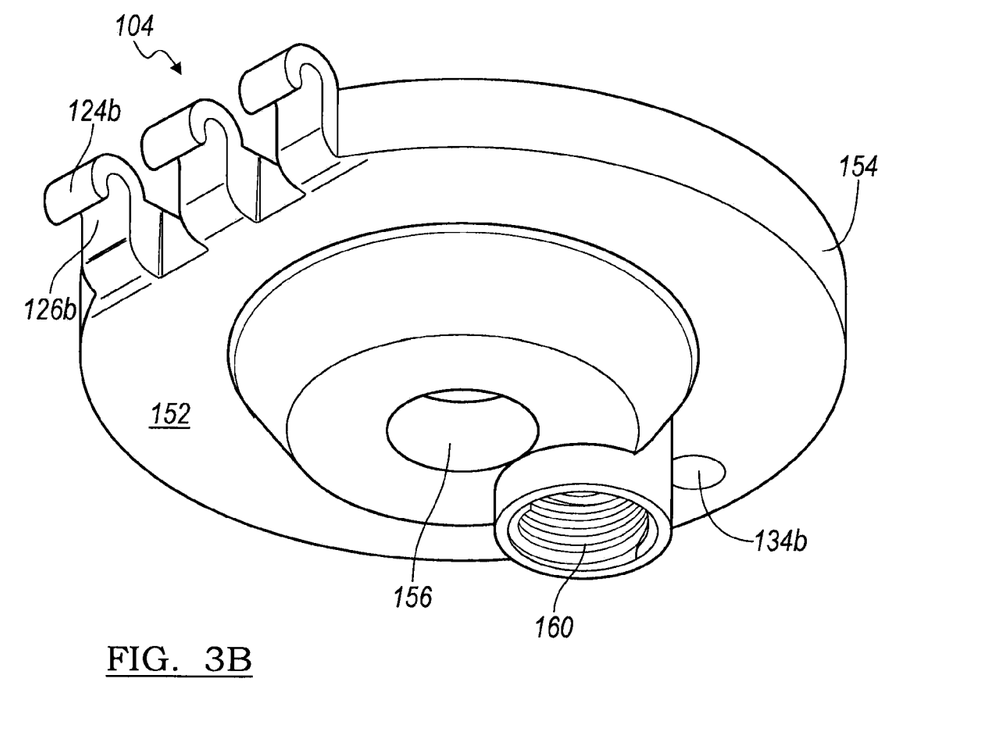
FIG. 3B depicts an exterior view of a second portion of the head mold component according to various embodiments.

With reference to FIGS. 3A and 3B, the head component second mold portion 104 includes an inner surface 150, an outer surface 152, and a connection component 124b defining hook-shaped passages 126b therein. The perimeter of the head component second mold portion 104 forms an edge 154 which surrounds a recessed region 156 which extends downwardly from the outer surface 152 and forms the cavity portion 106b. The outer surface 152 is flat relative to the raised region 132 of the first portion 102 as shown in FIG. 1 to provide the appropriate shape for the lower region of the femoral head 300 as depicted in FIG. 9B. Returning to FIGS. 3A and 3B, the recessed region 156 includes a cylindrical interior raised ring or lip 158 in which the head connector 110 cylindrical region 119 may be retained by an o-ring (not shown) and further secured by the abutment member 117 as best shown in FIG. 1.

Returning to FIGS. 3A and 3B, the outer surface 152 of the head component second mold portion 104 further includes a threaded opening 160 or filling port which functions in multiple capacities as will be detailed later herein. The head component second mold portion defines an internally threaded opening 134b.

The head component second mold portion 104 and the recessed portion 156 provide surface features 162 which, upon filling the head component mold 100, provide depressions 302 in the articulating head 300 of the final implant, as shown in FIG. 9B, which are the negative impression of the surface features 162. While surface features which form positive impressions can be used on the implant, those forming negative impressions facilitate easy removal of the temporary implant by preventing a potentially positive impression from becoming lodged into a tissue. The resultant depressions 302 increase the surface area of the resultant articulating head 300. Suitable depressions 302 include, but are not limited to grooves, dimples, hemispheres, cones, stars, ridges, notches, and the like. The depressions 302 can also include individual letters or combinations of letters and designs, such as a logo or part number.

It is understood that in such embodiments, the surface features 162 can be included on either of the head component first mold portion 102 or the head component second mold portion 104. The surface area of the temporary implant 300 can be increased by from about 1% up to 50% or more depending on the combination of surface area increasing features 162 employed in the mold 100. An exemplary, but non-limiting, benefit of the increased surface area is the increased amount of antibiotic or other therapeutic material (i.e.: drugs, vitamins, etc.) from the surface of the temporary implant to the defect site. The increased delivery of the antibiotic or other therapeutic material expedites healing and minimizes the recovery time of the patient.

Figure 5A:
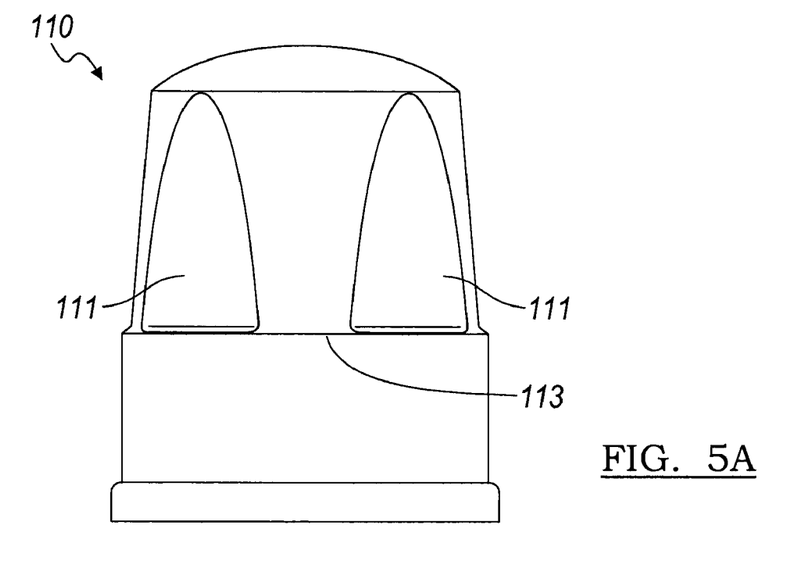
FIGS. 5A-5B depict various views of a head connector portion according to various embodiments.
Figure 5B:
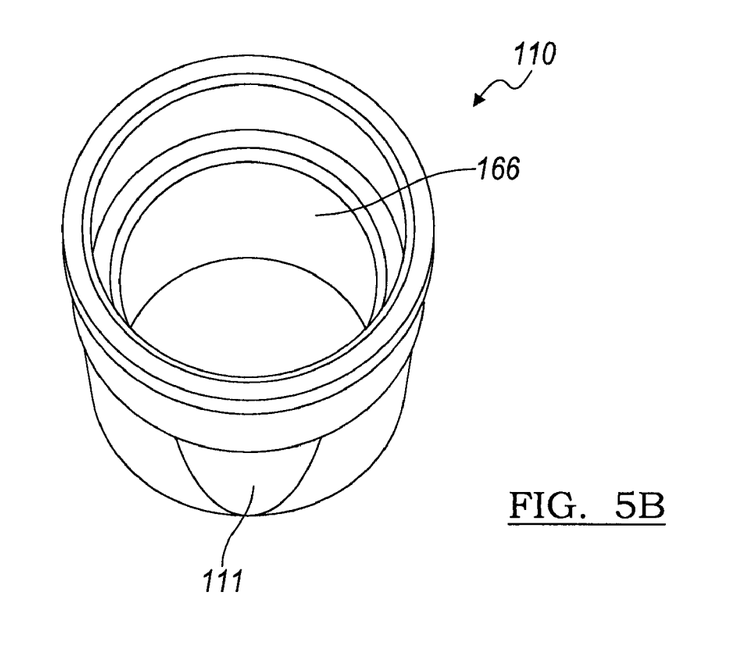

Referring to FIGS. 1 and 5A-5B, the head connector 110 can define a hollow chamber (shown in phantom) formed by a metal insert contained within the head component mold 100. The head connector 110 exterior surface defines flats 111 to assist in the fit of the head connector 110. In addition, the flats 111 prevent the rotation of the head connector 110 in the cement. The head connector interior surface defines a shoulder 113 which mimics the outer contour of the head connector. The shoulder 113 sits atop the head connector alignment member 112 as will be detailed later herein. Exemplary metals for the head connector 110 include stainless steel, titanium, cobalt, and the like and various alloys thereof. The head connector 110 can mate with the femoral stem component using a taper fit, such as a Morse taper, as a non-limiting example. The head connector 110 can optionally include surface roughening features or a surface texture to facilitate placement and fit with the stem implant 400.

In various embodiments, the head connector 110 is a female connector and is contained within the head component mold 100 such that upon filling the head component mold 100 with a material, such as a bone cement, a void volume will be defined in the articulating head portion of the temporary implant having a volume that is roughly equivalent to the void volume defined by the head connector 110. In still other embodiments, the head connector 110 can be a male connector and is contained at a region of the head component mold 100 and does not define a hollow region within the head component mold 100 upon filling the head mold with the material.

In either embodiment, the head connector 110 is fixed in the head component mold 100 so that it is not inadvertently displaced. The fixation of the head connector 110 is facilitated by the head connector alignment member 112. Further the head connector alignment member 112 can be made of a material which facilitates easy removal of the head connector alignment member 112 from the head connector 110. In various embodiments, the head connector alignment member 112 can be formed of a polymer material, such as polyethylene or PEEK. The head connector alignment member 112 can be formed of the same material as the head component mold 100 or it can be made of a different material.

The head connector alignment member 112 includes a tapered region 115, an abutment member 117, and a cylindrical region 119. As depicted, the head connector alignment member 112 can be hollow. The tapered region 115 mates with the interior region 166 of the head connector 110. The abutment member 117 is sized to extend beyond the perimeter of the opening 158 to prevent the tapered region 115 from passing therethrough. The head connector alignment member 112 is retained in the head component second mold portion 104 by a lip 158 or ring about the interior region 156 of the head component second mold portion 104. The lip 158 and the head connector alignment member 112 can be maintained in contact using friction between the materials. Any other suitable retention technique can also be employed in accords with the present teachings.

Inclusion of the head connector alignment member 112 in the head component mold 100 helps maintain a material-tight integrity of the head component mold 100 and prevents leakage of a filling material therefrom. Further, in various embodiments, the hollow alignment member 112 facilitates access to the head connector 110 and allows a user to press against the head connector 110 to free the implant from the mold 104. In various embodiments, the head component mold 100 and the head connector alignment member 112 can be provided as a single unit. The head connector alignment member 112 is used for temporary securing purposes only and is not included in the final articulating head implant 300.

To connect the head component mold first portion 102 with the head component second mold portion 104, the offset connection components 124a and 124b are interlaced to form a piano hinge which is connected over the pin or rod 128. The pin 128 is placed through the openings 126a formed in the connection component 124a of the head component mold first portion 102. This can be achieved by providing a pin 128 which has previously been insert molded into the openings 124a. Next, the pin 128 is hooked underneath the hook shaped passages 126b to removably connect the head component mold first portion 102 with the head component second mold portion 104. In addition, the removal of the pin 128 allows head 300 to be removed from portion 104.

Further, with reference to FIG. 1, the head component mold first portion 102 and second portion 104 can be secured together by disposing a screw 136 through the openings 134a and 134b, which are concentric and align when the head component mold first portion 102 and head component mold second portion 104 are interlaced at the connection components 124a and 124b. It is understood that although a single pair of openings 134a and 134b are provided, the head component mold 100 could include multiple pairs of matching openings placed around the perimeter 130 and perimeter 154 of the head component mold 100. As detailed later herein, the opening 134a is manipulated to provide a mechanical advantage to separate the implant from the head component mold first portion 102 and head component mold second portion 104.

The threaded opening 160 in the head component second mold portion 104 provides an access through which to deliver a material to fill the head component mold 12. It is understood that the threaded opening 160 can be defined at any region of the head component mold 100 and is not limited to placement on the second mold portion 104. The threaded opening 160 can be sized to accommodate a nozzle of a delivery device or a syringe through which a material is delivered to the head component mold 100.

Figure 4A:
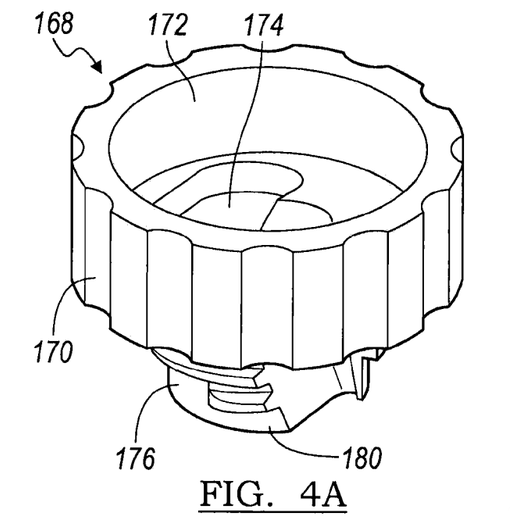
FIGS. 4A-4C depict various views of a self-cleaning cap according to various embodiments.
Figure 4B:
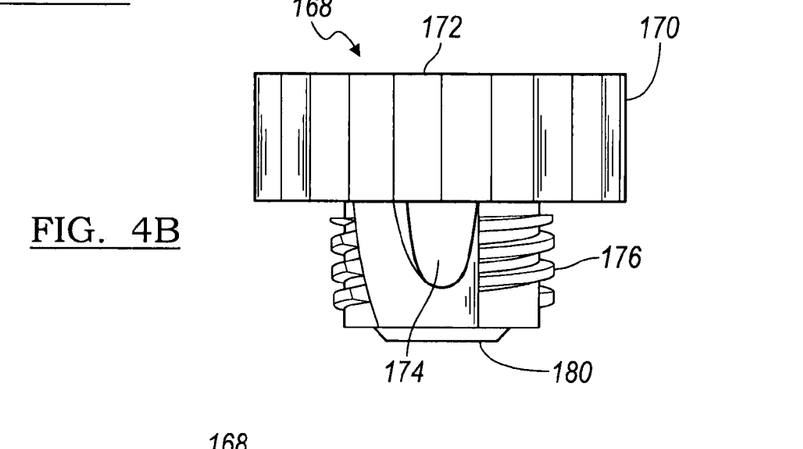
Figure 4C:
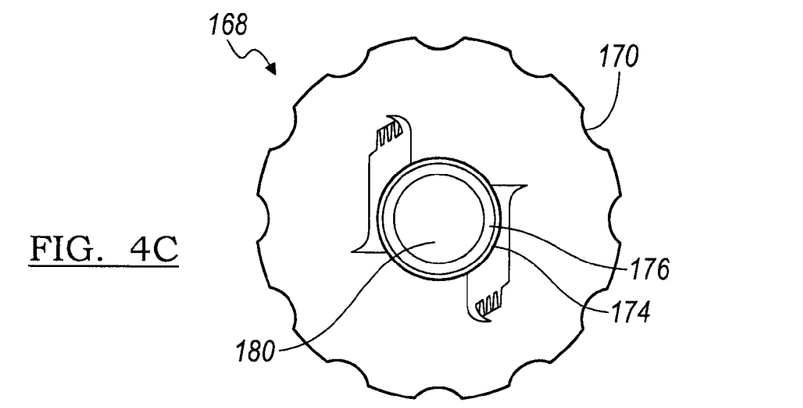

Turning to FIGS. 4A-4C, a self-cleaning cap 168 is provided. The self-cleaning cap 168 helps to provide a flush region on the implant 300 or 400 by removing, blocking, or segregating excess material to escape from the respective mold 100 or 200. Further, the self-cleaning cap can relieve the excess material or cement which may be delivered using high pressure delivery devices. The self-cleaning cap 168 includes a head 170 which defines a containment region 172. The self-cleaning cap 168 further defines a threaded region 176 which defines fluted or interrupted hollow regions 174 and terminates in a closed bottom 180. The threaded region 176 can mate with the threaded opening 160 defined by the head component mold second portion 104, as shown in FIG. 1. As the self-cleaning cap 168 is advanced through the threaded opening 160, any excess material contained in the head component mold 100 passes around the closed bottom 180, up through the interrupted hollow regions 174, and into the recessed containment region 172. Accordingly, the excess material can be easily separated from the final implant and prevents the excess material from becoming an unwanted plug or anchor to undesirably secure the temporary implant to the mold. The self-cleaning cap 168 helps to prevent overfilling the mold 100 and allows the operator to remove any excess material. The self-cleaning cap 168 provides a flush implant and cleans the threaded opening 160. As shown in FIG. 9B, the closed bottom 180 of the self-cleaning cap 168 can leave an impression 304 in the implant.

Turning to FIG. 6, the stem component mold 200 includes a stem component first portion 202 and a stem component second portion 204. Similar to the head component 100 as detailed above, each portion 202 and 204 generally forms a portion of a "clamshell" and define cavity portions 206a and 206b, respectively, such that upon connecting and closing the components of the stem component mold 200, the area between the cavity portions 206a and 206b accommodate the cement, a stem insert 210, and a stem component alignment screw 212.

Figure 7:
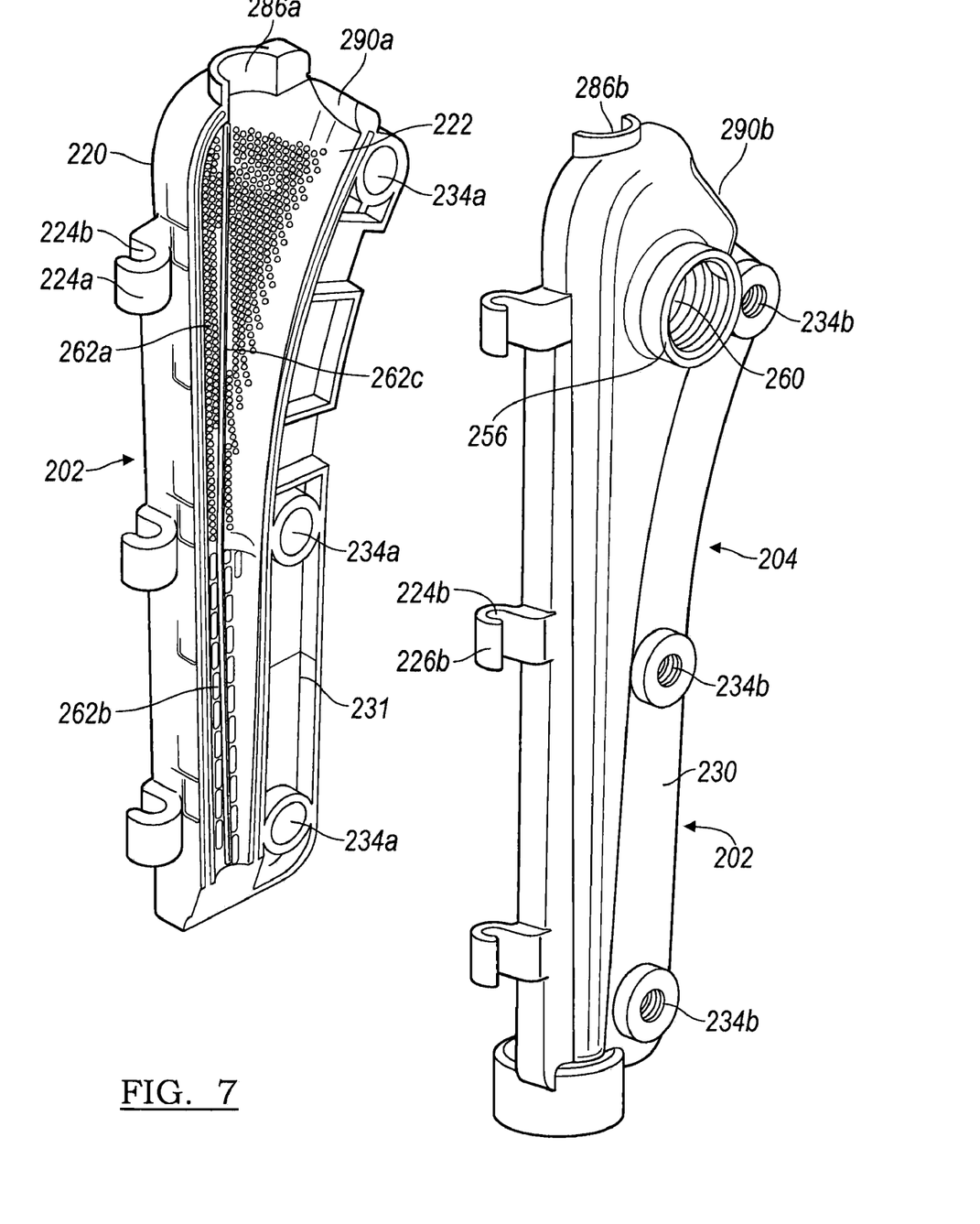
FIG. 7 depicts an exploded view of a stem mold component according to various embodiments.

Referring to FIGS. 6 and 7, the stem component mold first portion 202 includes an outer surface 220, an inner surface 222, and a connection component 224a which further defines a series of hooks 226a to accommodate connection component pins 228. As stated above, the connection component pins 228 can be molded into the connection component 224a. It is further understood that a single connection component pin can also be used. The stem component mold first portion 202 also includes a perimeter or edge 230. The proximal end of the stem component mold first portion 202 defines a fixation screw 212 receiving region portion 238a. The perimeter 230 defines a plurality of screw receiving openings 234a dispersed therein.

As shown in FIG. 7, the inner surface 222 includes a plurality of surface features 262a, 262b, and 262c which upon filling the stem component mold 200, provide depressions 402a, 402b, and 402c in the femoral stem 400 of the final implant as shown in FIG. 10, which are the negative impression of the surface area increasing features 262a, 262b, and 262c. It is understood that the location of the surface features 262a, 262b, and 262c are not limited to being only on the stem component mold first portion 202.

As illustrated, the surface features 262a are raised protrusions which will form dimples 402a in the femoral stem 400 at a proximal region 410 of the femoral stem implant 400, as shown in FIG. 10. The surface features 262b shown in FIG. 6 are linear raised dashes which will provide depressions 402b on the distal region 412 of the femoral stem implant 400 as shown in FIG. 10. The difference between the surface features 262a and 262b provides a dual grip to allow a tighter hold at the proximal region 410 of the femoral stem 400 where the surface features 262a are smaller and more densely placed and a looser hold at the distal region 412 where the surface features 262b are elongated or larger and provided in a lesser density. The longitudinal surface features 262b are disposed such that they align with the axis of the femoral stem to facilitate easy removal of the temporary implant 400. The surface feature 262c is a linear raised ridge or ledge that forms a venting area 402c which extends the length of the mold portions 202 and 204 to provide ventilation in the femoral stem 400 to allow trapped air to escape past the femoral implant 400 upon insertion into a patient and prevent a vacuum upon explanting of the implant. It is understood that although the raised ridge or ledge surface feature 262c is depicted as a continuous ridge or ledge, the ventilation feature can also be provided if the surface feature 262c was provided in several segments which extend longitudinally along the mold portions 202 and 204.

The surface features 262a, 262b, and 262c detailed here are merely exemplary, and it is understood that any combination of surface features or single-type of surface features can be used within the scope of the present teachings, including the types of surface features detailed with respect to the head component mold 100. Further, similar to the surface features used with the head component mold 100, the various surface features 262a, 262b, and 262c of the stem component mold 200 provide an increase in the surface area of the femoral implant 400 which includes the exemplary, but non-limiting, benefit of the increased amount of antibiotic or other therapeutic material (i.e.: drugs, vitamins, etc.) from the surface of the temporary implant 400 to the patient to thereby expedite healing and minimize the recovery time of the patient.

Figure 12A:
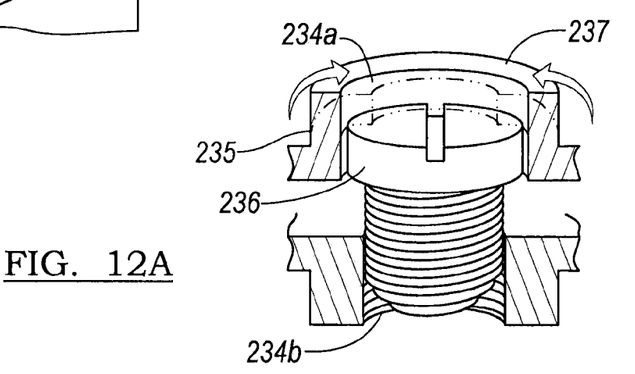
FIGS. 12A-12B depict a self-separating mechanism according to various embodiments.
Figure 12B:
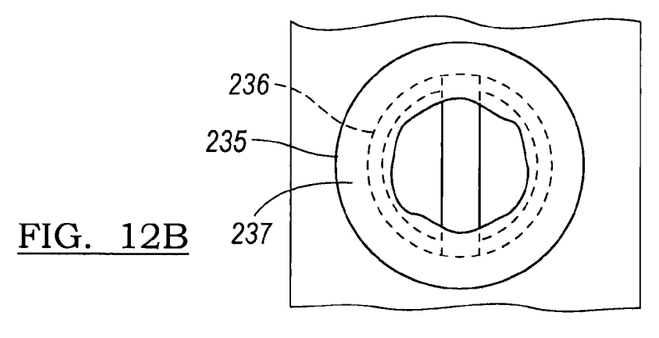

The stem component mold second portion 204 is generally a mirror image of the stem component mold first portion 202 with a few additions. The stem component mold second portion 204 includes an inner surface 254, an outer surface 256, and a connection component 224b which further defines a series of hooks 226b to accommodate the connection component pin 228. The perimeter of the stem component mold second portion 204 forms an edge 231. A threaded opening 260 is provided on the outer surface 256 which functions in multiple capacities as will be detailed later herein. The proximal end of the stem component mold second portion 204 defines a fixation screw 212 receiving region portion 238b. The stem component mold second portion 204 perimeter 231 defines a plurality of screw receiving threaded openings 234b dispersed therein. In various embodiments, the openings 234b include a sonically inserted metal nut (not shown) to receive the screw 212. Similar to the head component 100, the screw receiving openings 234a define ledges 235 which can be manipulated to provide a fold-over 237 (FIGS. 12A and 12B) to rotatably trap the screws 236, and the openings 234a align with threaded openings 234b.

Figure 8:
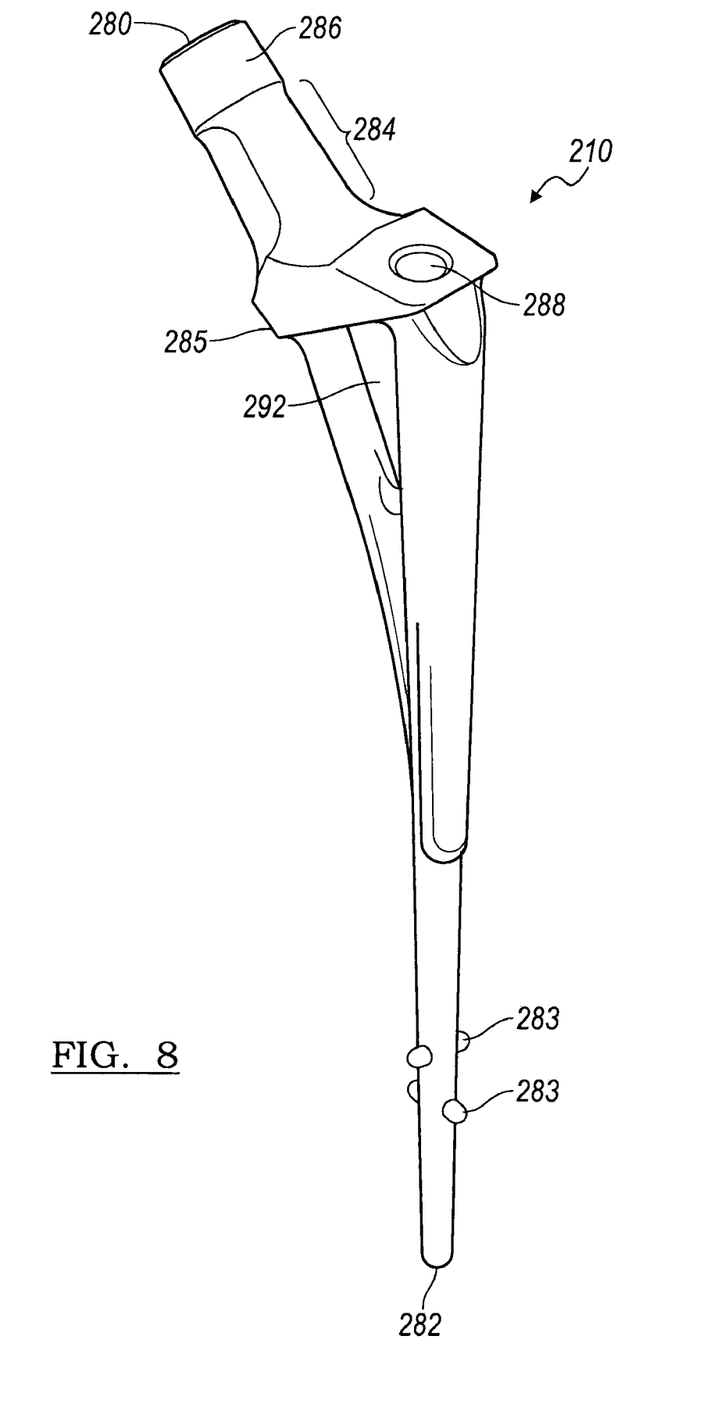
FIG. 8 depicts a perspective view of a femoral stem insert according to various embodiment.

Turning to FIG. 8, the stem insert 210 provides a reinforcing element for the stem implant 400 as shown in FIG. 10. Returning to FIGS. 6 and 8, the stem insert 210 includes a proximal end 280, a distal end 282, at least one distal end spacer 283, and a ledge or flange 285. The stem insert 210 is shaped to follow the general contour of the stem component cement mold 200 as shown in FIG. 6 and can generally extend the length of the stem component cement mold 200. The distal end spacers 283 set off the stem insert 210 from the sides or walls of the cavity and maintain proper alignment thereof.

Returning to FIG. 8, at a mid-region of the stem insert 210 there is a dispersion region 292 which is a hollow region or void of the stem insert 210. The dispersion region 292 provides a passage for the material to flow around the stem insert 210 to completely fill the cavity up to the flange 285 defined by the stem insert 210. The stem insert 210 can be made of any suitable material including polymers and metal. In embodiments where the stem insert 210 is made from a metal, such as titanium, the stem insert 10 connection region 210 can be mated with the head connector 110 which is disposed within the head component 300. In various embodiments, the connection region 210 may be mated to the head connector 110 via a taper adapter (not shown). The taper adapter may come in various lengths in order to allow for the correct head height adjustment in order to ensure the implant fits the patient's anatomy.

The stem insert 210 includes a stem neck portion 284 and a stem connector 286. The stem neck portion 284 is designed to fit between the opening formed when the curved recessed regions 290a and 290b of the stem mold first component 202 and stem mold second component 204 are joined. The stem connector 286 can be in the form of a Morse taper through which to connect to the head connector portion 110 of FIG. 9B. Returning to FIGS. 6 and 8, in various embodiments, the stem connector portion 284 can also include surface roughening features or a surface texture to facilitate placement and fit of the stem connector portion 284 with the head connector portion 110 of FIG. 9B. It is understood that the stem insert 210 can be made in differing lengths and widths to provide further customization of the temporary implant depending on the patient's needs.

With further reference to FIGS. 6 and 8, the stem insert 210 further defines a securing screw 212 receiving opening 288. When the stem insert 210 is disposed with in the assembled mold portions 202 and 204, the securing screw 212 can be advanced through the opening formed between elements 238a and 238b and down into the opening 288. The securing screw 212 fixes and holds the stem insert 210 in a stationary position within the cavity. In addition, the securing screw 212 also prevents the threads of the inserter/extractor from flowing cement.

To connect the stem component mold 200 together, the rod 228 is passed through the alternating hook shaped openings 224a and 224b of the opposing stem component mold portions 202 and 204, respectively, as shown in FIG. 6. As explained above, the rod 228 may be insert molded into the mold portions 202. Similar to the description above, the arrangement provides a piano hinge for the stem mold component 200 by which to open or close the stem component mold 200.

The present teachings further provide methods of providing and using the modular cement mold. Although the methods are disclosed as used with certain embodiments of the present teachings, it is understood that the methods disclosed can be used with any of the mold embodiments detailed above herein.

First, a surgeon or assistant will mix the appropriate antibiotic loaded cement or add an antibiotic to the particular cement. It is understood that the preparation of the cement is performed according to the label instructions of the particular cement. For example, about two grams of antibiotic are mixed with each 40 gram packet of bone cement powder which is then mixed with a corresponding number of 20 milliliter ampoules of a liquid monomer. The bone cement can be a poly-methyl-methacrylate (PMMA) cement such as those produced under the trade names Generation 4™, CMW1, CMW2, CMW3, Zimmer Dough Type, or Zimmer LVC, or a MMA-styrene copolymer cement such as that produced under the trade names Howmedica, Simplex P, or Zimmer Osteobond, or an MMA-methyl acrylate copolymer such as that produced under trade names Cobalt™ G-HV or Cobalt™ HV sold by Biomet. Once the appropriate antibiotic loaded bone cement is mixed, the bone cement is put within a delivery device, such as a cement gun. It is understood that an adaptor may be employed to accommodate different types of delivery devices or cement guns.

The appropriately sized mold portions 102 and 104 and mold portions 202 and 204 along with the related appropriately sized components, such as the head connector 110 or stem insert 210 are selected to form a customized fit for both the articulating head 300 and femoral component 400. It is understood that the head component 300 and the stem component 400 can be varied in size to provide further customization of the temporary implant depending on the patient's needs. The modular systems of the present teachings can be provided as a plurality of differently sized head components 100, stem molds 200, and related subcomponents. Once the appropriately sized components are selected, a surgeon will generally grasp the head component mold 100 and threadedly engage the nozzle of the delivery device into the access port 160. With the nozzle substantially sealing the access port 160, the surgeon will engage the delivery device to dispense out the bone cement within the inner cavity 106a and 106b formed within the head component mold 100. After removing the cement delivery device, the surgeon then secures the self-cleaning cap 168 into the opening 160. Any excess cement will extrude out of the self-cleaning cap 168 and facilitate providing a flush implant.

The assembled mold 200 is connected as follows. It is understood that in various embodiments, the mold 200 can be provided pre-assembled or partially pre-assembled where some components must be connected by the user prior to use. In the assembled device, the stem component mold first portion 202 and stem component mold second portion 204 are connected using the connector 228 which is interlaced between the series of offset hooks 226a and 226b. The stem insert 210 is then aligned in the cavity formed from elements 206a and 206b and secured via fixation member 212. The recess or dispersion region 292 of the stem insert 210 is arranged to be aligned with the opening 260 defined in the stem component mold second portion 204 to provide proper flow of the material around the stem insert 210. The stem insert 210 is then fixed into the mold portions 202 and 204 using the screw 212. The stem component mold first portion 202 and second portion 204 are then secured with the screws 236 in each respective pair of bores 234a and 234b. As mentioned above, and as shown in FIGS. 12A and 12B, the ledges 235 can be heated or otherwise manipulated to provide the fold over region 237 by which to rotatably trap the screw 236 therein. The fold over region 237 can also be provided as pre-folded over the screw 236 and alleviate the need for manipulation of the fold over region 237. The user then delivers the bone cement within the inner cavity 206a and 206b to the through opening 260. The self-cleaning cap 168 is then fixed within the opening 260, and the excess bone cement will extrude through the openings 174 defined in the self-cleaning cap 168.

Once the head component mold 100 and stem component mold 200 are filled, the assemblies can be placed on a nearby surface, such as a surgical table, to allow the cement to cure and cool while the surgeon moves on to another task, thereby substantially increasing the efficiency and reducing the time for the surgical procedure. Once the bone cement has sufficiently cured, the surgeon can grasp the head mold component 100 and remove the screw 136 disposed in the opening formed by elements 134a and 134b. The user attempts to back the screw 136 out of the threaded opening 134b and towards the ledge 135. The screw 136 then engages the ledge 135 and fold-over region 137 and is prevented from passing beyond the fold-over region 137 and back through the opening 134a. The retention force of the ledge 135 and fold-over region 137 against the rotating screw 136 pries the two mold component portions 102 and 104 apart to free the implant. Similarly, the surgeon removes any other screws 236 from the openings formed by the pairs of bores 234a and 234b using leverage from the ledges 235 and fold-over regions 237.

The stem component 400 of the temporary hip implant can then be simply engaged in the intramedullary canal of the host femur. The air vent 402c formed in the stem component 400 facilitates the passage of air from within the host femur to be expelled upon insertion of the stem component 400.

The head component 300 is then disposed over the stem connector 286 via the head connector 110, and the temporary implant is assembled. This implanted head component 300 and stem component 400 allow the distended joint to be subsequently re-engaged with the temporary implant to enable limited non-load bearing movement by the patient. The temporary implant allows the patient to generally sit up or be transported out of a hospital during the temporary recovery stage prior to having a revision type prosthesis subsequently implanted. During this time the antibiotic in the bone cement leaches out to the infected area and soft-tissue tension is maintained.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A modular articulating cement spacer mold for forming a temporary implant comprising:
    a. a mold first portion;
    b. a mold second portion;
    c. a hinge region connecting the mold first portion and the mold second portion; and
    d. a self-separating device secured to the mold first portion and the mold second portion, the self-separating device configured to removably secure the mold first portion and the mold second portion when the self-separating device is in a first position, and the self-separating device configured to separate the mold first portion and the mold second portion when the self-separating device is in a second position.

2. The modular articulating cement spacer mold of claim 1, wherein the temporary implant comprises at least a portion of a hip implant.

3. The modular articulating cement spacer mold of claim 1, wherein the hinge region defines a piano hinge and further wherein the hinge region is defined by portions of the first mold portion and the second mold portion.

4. The modular articulating cement spacer mold of claim 1, wherein the mold first portion and the mold second portion respectively define a mold first portion peripheral edge and a mold second portion peripheral edge.

5. The modular articulating cement spacer mold of claim 4, wherein the self-separating device comprises a cavity defined by the mold first portion peripheral edge to rotatably receive and capture a region of a screw and a threaded bore defined by the mold second portion to secure the screw.

6. The modular articulating cement spacer mold of claim 1, wherein the self-securing device comprises a deformable ledge covering a screw to prevent retraction thereof.

7. A modular articulating cement spacer mold for forming a temporary implant comprising:
    a. a mold first portion and a mold second portion defining interior surfaces and a cavity therebetween, wherein at least one of the mold first portion or mold second portion define an internally threaded port;
    b. a hinge region connecting the mold first portion and mold second portion;
    c. a self-securing device configured to removably secure and the mold first portion and the mold second portion when the self-securing device is in a first position, and the self-securing device configured to separate the mold first portion and the mold second portion when the self-securing device is in a second position;
    d. a ventilation forming surface feature on the interior surface of at least one of the mold first portion or the mold second portion;
    e. a plurality of a first surface feature and a plurality of a second surface feature located on the interior surface of at least one of the mold first portion or the mold second portion, wherein the density of pluralities of surface features decreases from a proximal end of the mold toward the distal end; and
    f. a self-cleaning element which selectively blocks the mold cavity and is mateable with the internally threaded port.

8. The modular articulating cement spacer mold of claim 7, wherein the mold is shaped as a portion of a hip implant.

9. The modular articulating cement spacer mold of claim 7, wherein the surface features include a plurality of dimples and a plurality of dashes.

10. The modular articulating cement spacer mold of claim 7, wherein the ventilation forming surface feature comprises a raised longitudinal ledge which extends along the interior surfaces of the mold and extends from a proximal end of the mold to a distal end of the mold.

11. A modular articulating cement spacer mold for forming a temporary implant comprising:
    a. means for accessing an interior surface of the cement spacer mold;
    b. means for excluding a material from an interior cavity of the cement spacer mold;
    c. means for providing differing adhesion properties of the temporary implant; and
    d. means for providing ventilation to a region of the temporary implant;
    wherein the means for accessing the interior surface of the cement spacer mold comprises a self-separating device secured to a mold first portion and a mold second portion, the self-separating device configured to removably secure the mold first portion and the mold second portion when the self-separating device is in a first position, and the self-separating device configured to separate the mold first portion and the mold second portion when the self-separating device is in a second position.

12. The modular articulating cement spacer mold of claim 11, wherein the means for segregating a material from an interior region of the cement spacer mold comprises a self-cleaning element which selectively blocks the mold interior cavity and is mateable with an internally threaded port defined by the mold.

13. The modular articulating cement spacer mold of claim 11, wherein the means for providing different adhesion properties of the temporary implant comprises a plurality of first surface features and a plurality of second surface features on a region of the interior surface of the cement spacer mold.

14. The modular articulating cement spacer mold of claim 11, wherein the means for providing ventilation to a region of the temporary implant comprises a ventilation forming surface feature which extends from a distal end to a proximal end of the interior surface of the cement spacer mold.

* * * * *

UNITED STATES PATENT AND TRADEMARK OFFICE
CERTIFICATE OF CORRECTION

PATENT NO. : 8,206,143 B2
APPLICATION NO. : 12/390084
DATED : June 26, 2012
INVENTOR(S) : H. Gene Hawkins et al.

Page 1 of 1

It is certified that error appears in the above-identified patent and that said Letters Patent is hereby corrected as shown below:

In the Specification

Column 2, line 4, "a interior" should be --an interior--.

Column 2, line 22, "embodiment" should be --embodiments--.

Column 9, line 31, "with in" should be --within--.

Column 9, line 63, "4$^{TM}$" should be --4(TM)--.

Column 10, line 1, both occurrences of "Cobalt$^{TM}$" should be --Colbalt(TM)--.

In the Claims

Column 12, lines 12-13, Claim 7, after "secure" delete "and".

Signed and Sealed this
Twenty-second Day of October, 2013

Teresa Stanek Rea
*Deputy Director of the United States Patent and Trademark Office*